US010012653B2

(12) United States Patent
Zheng et al.

(10) Patent No.: US 10,012,653 B2
(45) Date of Patent: Jul. 3, 2018

(54) NANOPARTICLES FOR TARGETING ACID TUMOR MICROENVIRONMENTS (75) Inventors: Jie Zheng, Allen, TX (US); Mengxiao Yu, Frisco, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 370 days.

(21) Appl. No.: 14/124,057

(22) PCT Filed: Jun. 14, 2012

(86) PCT No.: PCT/US2012/042525
§ 371 (c)(1),
(2), (4) Date: Mar. 17, 2014

(87) PCT Pub. No.: WO2012/174287
PCT Pub. Date: Dec. 20, 2012

(65) Prior Publication Data
US 2014/0193837 A1    Jul. 10, 2014

Related U.S. Application Data (60) Provisional application No. 61/497,471, filed on Jun. 15, 2011.

(51) Int. Cl.
| | | |
|---|---|---|
| C09K 11/58 | (2006.01) |
| B82Y 15/00 | (2011.01) |
| G01N 33/58 | (2006.01) |
| G01N 33/543 | (2006.01) |
| A61K 49/00 | (2006.01) |
| B82Y 5/00 | (2011.01) |

(52) U.S. Cl.
CPC ....... *G01N 33/587* (2013.01); *A61K 49/0065* (2013.01); *G01N 33/54346* (2013.01); *B82Y 5/00* (2013.01); *B82Y 15/00* (2013.01); *C09K 2211/188* (2013.01); *Y10S 977/773* (2013.01); *Y10S 977/92* (2013.01)

(58) Field of Classification Search
None
See application file for complete search history.

(56) References Cited

U.S. PATENT DOCUMENTS 7,507,530 B2 *  3/2009  Huang ............. A61K 47/48861
                                                      422/68.1
8,815,158 B2 *  8/2014  Zheng ................ A61K 49/0017
                                                      422/82.07
2005/0118252 A1  6/2005  Bae et al.
2005/0277739 A1  12/2005  Yang et al.
2008/0233107 A1 *  9/2008  Reshetnyak ......... A61K 9/0019
                                                      424/130.1
2009/0068505 A1  3/2009  Adzic et al.
2009/0226376 A1  9/2009  Grimmond et al.
2010/0075339 A1  3/2010  Rector et al.
2010/0260686 A1  10/2010  Zhang et al.
2011/0105437 A1  5/2011  Ralph et al.
2011/0111518 A1  5/2011  Zheng et al.
2011/0123452 A1 *  5/2011  Hainfeld ............ A61K 41/0038
                                                      424/9.1
2011/0269170 A1 * 11/2011  Kim ................... A61K 41/0052
                                                      435/29

FOREIGN PATENT DOCUMENTS

WO    WO 2009/064987    *  5/2009  ............. A61K 9/14

OTHER PUBLICATIONS

Zhou et al., Luminescent Gold Nanoparticles with Mixed Valence States Generated from Dissociation of Polymeric Au(I) Thiolates. J. Phys. Chem. C 2010, 114, 7727.*
Zhang et al., Fluorescence Quenching of CdTe Nanocrystals by Bound Gold Nanoparticles in Aqueous Solution. Plasmonics. Mar. 1, 2008; 3(1): 3-11.*
Vavere et al., A Novel Technology for the Imaging of Acidic Prostate Tumors by Positron Emission Tomography.. Cancer Res May 15, 2009 69; 4510.*
Shervedani et al., Functionalization of gold cysteamine self-assembled monolayer with ethylenediaminetetraacetic acid as a novel nanosensor. Analytica Chimica Acta 587 (2007) 254-262.*
Zheng et al., Different Sized Luminescent Gold Nanoparticles. Nanoscale. Jul. 21, 2012; 4(14): 4073-4083.*
PCT International Preliminary Report on Patentability, issued in International Application No. PCT/US2012/042525, dated Dec. 17, 2012.
PCT International Search Report, issued in International Application No. PCT/US2012/042525, dated Sep. 13, 2012.
Yu et al., "Luminescent gold nanoparticles with pH-dependent membrane adsorption", *J Am Chem Soc.*, 133(29):11014-11017, 2011.

* cited by examiner

*Primary Examiner* — Christopher M Babic
*Assistant Examiner* — Arthur S Leonard
(74) *Attorney, Agent, or Firm* — Parker Highlander PLLC (57) ABSTRACT

A composition is disclosed which is capable of being used for detection, comprising a noble metal nanoparticle. The inventive compositions exhibit little interaction with serum proteins while exhibiting pH-dependent adsorption onto live cell membranes. The nanoparticles of the claimed invention are capable of interacting with cell membranes, which in turn permits the advantages of nanoparticle bio-imaging to be extended to many pH dependent biological processes such as targeting acidic tumor microenvironment.

16 Claims, 4 Drawing Sheets

SEQUENCE LISTING

```
<160> NUMBER OF SEQ ID NOS: 1

<210> SEQ ID NO 1
<211> LENGTH: 38
<212> TYPE: PRT
<213> ORGANISM: Halobacterium salinarum
<220> FEATURE:
<221> NAME/KEY: PEPTIDE
<222> LOCATION: (1)..(38)

<400> SEQUENCE: 1

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35
```

NANOPARTICLES FOR TARGETING ACID TUMOR MICROENVIRONMENTS

CROSS-REFERENCES TO RELATED APPLICATIONS

This Application is a national phase application under 35 U.S.C. § 371 of International Application No. PCT/US2012/042525, filed Jun. 14, 2012, which claims the benefit under 35 U.S.C. § 119(e) of U.S. Provisional Patent Application Ser. No. 61/497,471 filed Jun. 15, 2011, the entire contents of which are hereby incorporated by reference.

STATEMENT REGARDING FEDERALLY-SPONSORED RESEARCH OR DEVELOPMENT

This invention was made with government support under Grant No. R21EB009853 awarded by the National Institutes of Health. The government has certain rights in the invention.

BACKGROUND OF THE INVENTION pH is a key parameter for many biological processes and also an important indicator for disease progression. For example, endocytosis, a process wherein substances are engulfed by cells, is involved with a pH change from neutral to acidic (pH 4.5-6.2). Due to the Warburg effect, the acidic pH is also characteristic of solid tumors (extracellular pH 6.0-7.0). Therefore, pH-responsive materials such as organic dye-based indicators, cationic polymers, and some peptides often serve as either tools in the fundamental understanding of cell biology or medicine for disease diagnosis and therapy. Nanoparticles often show broad and tunable optical, magnetic, electrical, photothermal properties, and a large surface-to-volume ratio, which allows the integration of different functional groups into one single entity. Therefore, nanoparticles showing pH-dependent interactions with live cells provide new multifunctional tools for disease diagnosis and therapy.

While metal nanoparticles hold great promise in bioimaging, drug/gene delivery, and phototherapy, their interactions with the cell membrane are generally insensitive to extracellular pH changes in a native biological environment because serum proteins are often adsorbed onto the metal nanoparticles and form a protein "corona". This protein corona, rather than surface ligands, governs interactions between nanoparticles and the cell membrane. Over 3700 proteins in the serum/plasma and their dynamic adsorption/desorption with the particles create great uncertainties in the rational manipulation of the nanoparticle-cell membrane interactions at different pHs.

Thus, it would be beneficial to create nanoparticles that are capable of interacting with cell membranes in different ways at different pHs, which in turn would allow the advantages of nanoparticle in bioimaging to be extended to many pH dependent biological processes. To address this challenge, the claimed invention comprises metal nanoparticles having little interaction with serum proteins while exhibiting pH-dependent adsorption onto live cell membranes. This simple surface chemical modification, where pH-dependent membrane adsorption is enabled, lends itself to biomedical applications of metal nanoparticles in the fundamental understanding of biological processes as well as disease diagnosis and therapy. The invention was made in part with support under Grant No. RP120588 awarded by the Cancer Prevention and Research Institute of Texas.

SUMMARY OF THE INVENTION

An embodiment of the invention is directed to a composition comprising a water-soluble fluorescent noble metal nanoparticle, a first anti-fouling ligand and a second pH-dependent ligand, wherein the noble metal nanoparticle is about 0.3 nm to 3 nm in diameter.

In certain embodiments of the invention, the anti-fouling ligand is glutathione. In other embodiments of the invention, the pH-dependent ligand comprises one or more thiol groups.

In certain embodiments of the invention, in addition to the anti-fouling ligand and the pH-dependent ligand, the nanoparticle further comprises a pH-dependent peptide such as pH low insertion peptide (pHLIP).

An embodiment of the invention is directed to a method of detecting a surface of a cell, the method comprising the steps of contacting a fluorescent noble metal nanoparticle-containing composition with a surface of a cell; adsorbing the composition comprising fluorescent noble metal nanoparticles on to the surface of the cell; and detecting the presence of the fluorescent nanoparticle on the surface of the cell.

BRIEF DESCRIPTION OF THE DRAWINGS

FIG. 1 shows (A) Absorption, excitation and emission spectra of glutathione-coated luminescent gold nanoparticles (G-AuNPs) and glutathione/cysteamine-coated luminescent gold nanoparticles (GC-AuNPs) in aqueous solution. G-AuNPs: One adsorption shoulder peak at 400 nm, $\lambda^{ex}_{max} = 300$ nm, $\lambda^{em}_{max} = 605$ nm; GC-AuNPs: Three adsorption shoulder peaks at 305, 375 and 450 nm, $\lambda^{ex}_{max} = 315$ nm, $\lambda^{em}_{max} = 575$ nm. Inset: Pictures taken under 365 nm UV excitation; (B) Typical transmission electron microscopy image of GC-AuNPs showing (C) a core size of 2.7±0.5 nm, and dynamic light scattering analysis showing a hydrodynamic diameter (HD) of 3.1±0.4 nm in aqueous solution;

FIG. 2 shows pH-dependent adsorption of GC-AuNPs on live HeLa cell membrane. Brightfield (A, C) and fluorescence (B, D) images of live HeLa cells incubated with 0.2 mg/mL GC-AuNPs at pH 7.4 (A, B) and pH 5.3 (C, D) in PBS at 25° C. for 10 min respectively (scalar bar, 20 µm). (E) Co-localization of GC-AuNPs with DiR (a phospholipid bilayer membrane dye) on live cell membrane (scalar bar, 20 µm);

FIG. 3 shows luminescence intensities of the cell membrane and zeta potentials of GC-AuNPs at different pHs. (A) Luminescence intensity of the cell membrane incubated with GC-AuNPs at different pH in PBS or in minimum essential medium (MEM) supplemented with 10% (v/v) fetal bovine serum (FBS) (Inset) respectively. (B) Zeta potentials of G-AuNPs and GC-AuNPs at pH 7.4 and pH 5.3 respectively. Results are presented as mean±SD (n=6)

DETAILED DESCRIPTION OF EXEMPLARY EMBODIMENTS

The claimed invention provides nanoparticle compositions comprising a fluorescent nanoparticle, methods for preparing the nanoparticle compositions and methods of using the nanoparticle compositions. The compositions of the present invention comprise noble metal nanoparticles, which are capable of fluorescing. The claimed invention provides for compositions comprising a water-soluble fluorescent noble metal nanoparticle. In an embodiment, the noble metal nanoparticle comprises between 2 and 1000 noble metal atoms. In preferred embodiments, the noble metal is selected from the group consisting of gold, silver, and copper.

Preferably the fluorescent nanoparticle of the claimed invention is capable of fluorescing over a pH range of approximately 3 to approximately 8.

In certain embodiments of the claimed invention, the surface of the fluorescent noble metal nanoparticle is modified to prevent fouling of the nanoparticle by nonspecific protein adsorption. In certain embodiments, the surface of the nanoparticle is coated with a ligand (anti-fouling ligand) that prevents adsorption of serum proteins on the surface of the nanoparticle and prevents fouling of the nanoparticle. In certain embodiments of the invention, the anti-fouling surface ligand is a protein or peptide. In other embodiments of the invention, the anti-fouling ligand is a polymer such as poly(ethylene glycol) (PEG) or oligo(ethylene glycol) (OEG). In certain embodiments of the invention, the anti-fouling ligand is a zwitterionic material such as sulfobetaine methacrylate (SBMA), carboxybetaine methacrylate (CBMA), poly(carboxybetaine acrylamide) (polyCBAA) or a mixed charge material. In certain embodiments of the invention the anti-fouling ligand is glutathione.

In an embodiment of the invention, the fluorescent noble metal nanoparticle is coated with a ligand (pH-dependent ligand) which modifies the surface of the nanoparticle to create a particle that allows the modified nanoparticle to bind to a cell membrane in mild acidic pH conditions (pH of 5.3 to 6.5). In certain embodiments of the invention, the pH-dependent ligand is a protonated ligand comprising one or more thiol groups. In certain embodiments of the invention, the pH-dependent ligand is cysteamine or cysteamine analogs. In other embodiments of the invention, the pH-dependent ligand is 3-amino-2-(aminomethyl) propane-1-thiol, 4-aminobenzenethiol, pyridine-4-thiol, 1-amino-5-methyl-1H-imidazole-2-thiol, 5-amino-2-mercapto-1-me-1H-imidazole-4-carboxan, aminopropane thiol, aminobutane thiol, aminoethane thiol, mercaptoethanol, mercaptopropanol, mercaptobutanol, mercaptoundecanol, (11-mercaptoundecyl) phosphonoperoxoic acid or 11-aminoundecane thiol.

In certain embodiments of the invention, the fluorescent noble metal nanoparticle binds to cell membrane surfaces in a pH-dependant manner.

In an embodiment of the invention, the fluorescent noble metal nanoparticle is coated with a first ligand and a second ligand. In certain embodiments of the invention, the first ligand is an anti-fouling ligand. In other embodiments of the invention, the second ligand is a ligand that exhibits pH-dependent membrane adsorption. In certain embodiments, the ratio of the first ligand to the second ligand on the surface of the fluorescent noble metal nanoparticle is 1:1, 1:0.75, 1:0.5, 1:0.25, 1:1.5, 1:2, 1: 2.5, or 1:3.

In certain embodiments of the invention, the pH-dependent ligand is hydrophobic. In embodiments of the invention, the hydrophobic pH-dependent ligand is 3-amino-2-(aminomethyl) propane-1-thiol, 4-aminobenzenethiol, pyridine-4-thiol, 1-amino-5-methyl-1H-imidazole-2-thiol, 5-amino-2-mercapto-1-me-1H-imidazole-4-carboxan, aminopropane thiol, aminobutane thiol, aminoethane thiol, mercaptoethanol, mercaptopropanol, mercaptobutanol, mercaptoundecanol, (11-mercaptoundecyl) phosphonoperoxoic acid or 11-aminoundecane thiol.

In certain embodiments of the invention, the fluorescent noble metal nanoparticle comprising a first anti-fouling ligand and a second pH-dependent ligand, further comprises a pH-dependent peptide or protein on the surface of the nanoparticle. In certain embodiments of the invention, the pH-dependent peptide or protein exists as an alpha-helix in mild acidic pH conditions (pH of 5.3 to 7.0) and translocates a conjugated moiety across the cell membrane when the extracellular pH is less than 7.0. In certain embodiments of the invention, the pH-dependent peptide comprises pH low insertion peptide (pHLIP) (SEQ ID NO:1).

The present invention further encompasses methods of using the fluorescent nanoparticle in order to study a biological state. The invention provides for a method of monitoring a molecule of interest by contacting the fluorescent noble metal nanoparticle with a sample containing the molecule of interest. In a preferred embodiment, the molecule of interest is present in a biological sample.

Unless otherwise noted, the terms used herein are to be understood according to conventional usage by those of ordinary skill in the relevant art. It is to be understood that as used in the specification and in the claims, "a" or "an" can mean one or more, depending upon the context in which it is used. Thus, for example, reference to "a cell" can mean that at least one cell can be utilized.

The present invention may be understood more readily by reference to the following detailed description of the preferred embodiments of the invention and the Working Examples included herein. However, before the present compounds, compositions, and methods are disclosed and described, it is to be understood that this invention is not limited to specific noble metals, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

As used herein, the term "noble metal" refers to the group of elements selected from the group consisting of gold, silver, and copper and the platinum group metals (PGM) platinum, palladium, osmium, iridium, ruthenium and rhodium. In certain preferred embodiments of the present invention, the noble metal is selected from the group consisting of gold, silver, and copper. In other preferred embodiments, the noble metal is silver. In other preferred embodiments, the noble metal is gold. In other preferred embodiments, the noble metal is copper.

As used herein, the term "nanoparticle" refers to an association of 2-1000 atoms of a metal. Nanoparticles may have diameters in the range of about 0.1 to about 3 nm. In other preferred embodiments, the nanoparticles comprise approximately 2-1000, approximately 2-500, approximately 2-250, approximately 2-100, approximately 2-25 atoms, or approximately 2-10 atoms.

As used herein, the term "water-soluble" refers to the ability to dissolve and/or form a suspension in an aqueous solution. While the fluorescent label may visibly dissolve in an aqueous solution, it is at least temporarily dispersible or capable of forming a suspension in an aqueous solution.

As used herein, the term "fluorescence" or "fluorescent" is a physical phenomenon based upon the ability of certain molecules to absorb and emit light at different wavelengths. The absorption of light (photons) at a first wavelength is followed by the emission of photons at a second wavelength and different energy. As used herein, a "fluorescent nanoparticle" is a molecule which absorbs light at a first wavelength and emits the photons at a second wavelength and different energy. As used herein, a "fluorescent label" is used interchangeably with a "luminescent label," and "fluorescent" and "fluorescence" are used interchangeably with the terms "luminescent" and "luminescence," respectively. As such, fluorescence is meant to include phosphorescence and Raman emission, and all emissions indicated by the term "luminescence." As used herein, the term "saturated fluorescence" refers to the ability of a molecule to fluoresce at all incident intensities. Preferably, the fluorescence is present on the surface of a noble metal nanoparticle. Preferably, the fluorescent molecules of the present invention fluoresce at a low excitation intensity, such as that provided by a mercury lamp. Preferably, the low excitation intensity is approximately 30 W/cm$^2$ at approximately 460 nm. In other embodiments, the excitation intensity can range from <1 W/cm$^2$ up to 10 kW/cm$^2$ at a range of excitation wavelengths from approximately 330 nm to approximately 900 nm. The excitation intensity can vary depending at least on the size of the nanoparticle, and the metal comprising the nanoparticle, and can be readily determined by one of ordinary skill in the art using methods well known in the art. While the fluorescent molecule as described herein is capable of fluorescing at a low excitation energy such as by a weak mercury lamp, in one embodiment the fluorescent molecule can fluoresce when activated by a laser.

As used herein, the term polypeptide refers to a chain of at least two amino acids joined by peptide bonds. The chain may be linear, branched, circular or combinations thereof. The terms "peptide," "polypeptide," and "protein" are used interchangeably herein. The terms do not refer to a specific length of the product. Thus, "peptides," "oligopeptides," and "proteins" are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide.

The present invention further encompasses methods for the preparation of the noble metal nanoparticle having the characteristics as described herein. In one embodiment, the method of preparing a noble metal nanoparticle comprises the steps of: a) combining an aqueous solution comprising a noble metal, and an aqueous solvent to create a combined solution; b) adding a first ligand; c) adding a second ligand; d) mixing the combined solution to allow the formation of a noble metal nanoparticle; e) adjusting the pH of the combined solution using acid or base.

In certain embodiments of these methods, a reducing agent is added to the combined solution to reduce the noble metal nanoparticle. Preferably the reducing agent is selected from the group comprising a chemical reducing agent, light, or a combination thereof. In certain embodiments of these methods, light can be used as a reducing agent to photoreduce the noble metal nanoparticles. In certain other embodiments of these methods, a chemical reducing agent can be used as a reducing agent. In one embodiment, light is used in combination with a reducing agent to photoreduce the noble metal nanoparticles.

Preferably, the aqueous solution comprising a noble metal ion used in the preparation of the compounds is selected from the group consisting of $AgNO_3$, $HAuCl_4.nH_2O$, and $CuSO_4.nH_2O$. In one embodiment, the aqueous solution comprising a noble metal is $AgNO_3$. In another embodiment, the aqueous solution comprising a noble metal is $HAuCl_4.nH_2O$. In a further embodiment, the aqueous solution comprising a noble metal is $CuSO_4.nH_2O$.

In one embodiment, the aqueous solution comprising a noble metal is $HAuCl_4.nH_2O$, a reducing agent is added to the combined solution along with a first ligand and a second ligand, the pH adjusted, and the combined solution is mixed for at least one hour to allow the formation of the gold nanoparticle. In another embodiment, the pH adjusted, combined solution is mixed for about 48 hours or longer (up to several months) to allow the formation of a fluorescent gold nanoparticle. In another embodiment, noble metal nanoparticles are created through photoreduction through irradiation with visible or ultraviolet light to allow the formation of a gold, silver or copper nanoparticle.

In an embodiment of the invention, the compositions of the invention are used to monitor the surface of cell membranes. In certain embodiments of the invention, the cell membranes that are targeted are tumor cell membranes.

WORKING EXAMPLES

Materials and Equipment

Organic dye DiR for staining phospholipid bilayer membrane was purchased from Invitrogen. Citrate-coated 20 nm gold nanoparticles were purchased from Ted Pella. All the other chemicals were purchased from Sigma-Aldrich and used as received unless specified. Particle size and zeta potential of nanoparticles in the aqueous solution were analyzed by a Brookhaven 90 Plus Dynamic Light Scattering Particle Size Analyzer (DLS) and a Brookhaven Zeta-PALS zeta potential analyzer, respectively. Transmission electron microscopy (TEM) images were obtained using a 200 kV Jeol 2100 transmission electron microscope. Absorption spectra were collected using a Varian 50 Bio UV-Vis spectrophotometer. The luminescence spectra were collected by a PTI QuantaMaster™ 30 Fluorescence Spectrophotometer (Birmingham, N.J.). FTIR spectra were obtained using a Nicolet Avatar 360 FTIR spectrometer. pH was measured by a Accumet AB15 pH meter and a Accuphast microprobe electrode.

Synthesis of Luminescent Gold Nanoparticles

Glutathione-Coated Luminescent Gold Nanoparticles (G-AuNPs) were synthesized by a self-dissociation of Au(I)-glutathione polymers in an aqueous solution. In a typical synthesis, a fresh aqueous solution containing reduced L-glutathione (25 mM) was added into a $HAuCl_4$ aqueous solution (25 mM) at a 1:1 molar ratio of gold to thiolated ligand. The solution was centrifuged at 21,000 g for 1 min. to remove the insoluble aggregates as well as large NPs. The supernatant was further purified by adding a small amount of ethanol into the aqueous solution (the ratio between water and ethanol is 2:1). Under such conditions, the luminescent gold NPs were precipitated out of the solution while the free GSH and gold ions remained in the solution. The precipitates were then resuspended in aqueous solution (DI water, PBS or 10% (v/v) FBS-containing MEM (without phenol red). The final solution contained G-AuNPs with diameter of ~2 nm. The pH of solution was adjusted by 1 M NaOH or 1 M HCl and then measured by a pH meter.

Glutathione and Cysteamine-Coated Luminescent Gold Nanoparticle (GC-AuNPs) were synthesized by a modified self-dissociation method to create luminescent gold nanoparticles with diversity in surface chemistry. A fresh aqueous solution containing reduced L-glutathione (12.5 mM) and cysteamine hydrochloride (12.5 mM) was added into a $HAuCl_4$ aqueous solution (25 mM), and macroscopic orange precipitate was formed immediately. After four weeks, the solution was then centrifuged at 21,000 g for 1 min. to remove the insoluble aggregates as well as large NPs. The supernatant was further purified by adding a small amount of ethanol into the aqueous solution (the ratio between water and ethanol is 2:1). Under this condition, GC-AuNPs were precipitated out of the solution. The precipitates were then resuspended in aqueous solution (DI water, PBS or 10% (v/v) FBS-containing MEM (without phenol red). The final solution contained GC-AuNPs with diameter of ~3 nm. The pH value of the solution was adjusted by 1 M NaOH or 1 M HCl and then measured by a pH meter.

Synthesis of Cysteamine-Coated Plasmonic Gold Nanoparticles (Non-luminescent)

Cysteamine-coated plasmonic AuNPs were prepared by the $NaBH_4$ reduction of $HAuCl_4$. Briefly, a fresh aqueous solution (150 μL) containing cysteamine hydrochloride (4.7 mM) was added to a $HAuCl_4$ aqueous solution (7.5 mM, 100 μL). The color of the solution turned from yellowish to cloudy orange, suggesting the formation of Au(I)-thiolate polymers. Aqueous solution containing $NaBH_4$ (10 mM, 20 μL) was quickly added to fully reduce the gold polymers until the color of 3 solution turned from orange to reddish, indicating the formation of plasmonic AuNPs. The AuNPs were purified by Sephadex-20 column.

Characterization of Surface Ligands on Glutathione and Cysteamine-coated Luminescent Gold Nanoparticles (GC-AuNPs)

The ratio of glutathione (GSH) to cysteamine (CA) on GC-AuNPs was calculated by analysis of FTIR spectra of GSH, CA, the mixture of GSH and CA at a 1:1 molar ratio and GC-AuNPs. To make a well mixed sample for FTIR spectrum measurement, GSH and CA were dissolved in aqueous solution at a 1:1 molar ratio and then freeze dried. The luminescent gold NPs were freeze dried for 24 hours.

The FTIR spectrum of CA was found to be different from that of GSH in a range of 1380-1900 $cm^{-1}$. GSH showed an obvious absorbance peak at 1714 $cm^{-1}$, originating from the C=O vibration of COOH group in GSH, while the peak at 1714 $cm^{-1}$ is absent from the spectrum of CA. On the other hand, CA exhibited strong absorbance at 1492 $cm^{-1}$, originating from the N-H vibration of $NH_2$ group in CA, and GSH showed low absorbance at 1492 $cm^{-1}$ (~19.1% of the absorbance at 1714 $cm^{-1}$). Therefore, the peak at 1714 $cm^{-1}$ can be considered as a characteristic peak for GSH, while CA has a characteristic peak at 1492 $cm^{-1}$.

Agarose Gel Electrophoresis

Britton-Robinson buffer solution at pH 5.3 or pH 7.4 was prepared as follows. Aqueous solution containing 0.04 M phosphoric acid, 0.04 M acetic acid and 0.04 M boric acid was prepared, and then 0.2 M sodium hydroxide was added to adjust the pH to 5.3 and 7.4 respectively.

The luminescent gold nanoparticles, G-AuNPs and GC-AuNPs were dissolved in Britton-Robinson buffer solution at pH 5.3 or at pH 7.4 containing 10% (v/v) fetal bovine serum (FBS) and then incubated in a 37° C. water bath for 30 min. As control samples, G-AuNPs and GC-AuNPs were dissolved in Britton-Robinson buffer solution at pH 7.4 or pH 5.3 and then incubated in a 37° C. water bath for 30 min. The samples were mixed with 3 μL 75% glycerol and then analyzed by 2% agarose gel electrophoresis using the Mini-sub cell GT Gel electrophoresis system (Bio-Rad Laboratories Inc.) and Britton-Robinson buffer solution at pH 5.3 or pH 7.4 with 7.5 V·$cm^{-1}$ for 30 min. Pictures were taken under the irradiation of 365 nm UV excitation.

Cell Culture

The cell line HeLa was purchased from ATCC (USA) and cultured in minimum essential medium (MEM) with 10% (v/v) fetal bovine serum (FBS) and 1% (v/v) penicillin-streptomycin (PS) at 5% $CO_2$ 37° C. Cells were plated in cell dishes with 14 mm glass coverslips and allowed to adhere for 48 h.

Microscopy Imaging

Interaction of Cysteamine-Coated Plasmonic AuNPs with Cell Membrane

Bright field live cell images were obtained by a BX-51 upright microscope (Olympus) with a 20×/0.46BD objective and an 18.2 Color Mosaic CCD camera (Diagnostic Instruments). Since the cysteamine-coated plasmonic AuNPs were not stable in PBS buffer, their interaction with cell membrane was performed by incubating the fixed HeLa cells with cysteamine-coated AuNPs in DI water at pH 7.4, pH 6.0 or pH 5.3 for 20 min at 25° C. The cells were rinsed with water before imaging.

Interaction of Luminescent AuNPs with Cell Membrane

Fluorescence and bright field live cell images were obtained by an IX-71 inverted fluorescence microscope (Olympus) with a 1.3 NA 100× oil-immersion objective under Hg-lamp excitation (for fluorescence imaging, Ex: 532-587 nm; Em: 605-682 nm; 30 W/$cm^2$; 2 s exposure time) and a Photon Max 512 CCD camera (Princeton Instrument). Live HeLa cells were rinsed with PBS buffer and incubated with G-AuNPs or GC-AuNPs in PBS or in 10% (v/v) FBS-containing MEM (without phenol red) at pHs 7.4, 6.0 or 5.3 at 25° C. (FIGS. 2A-D).

Figure 3A:
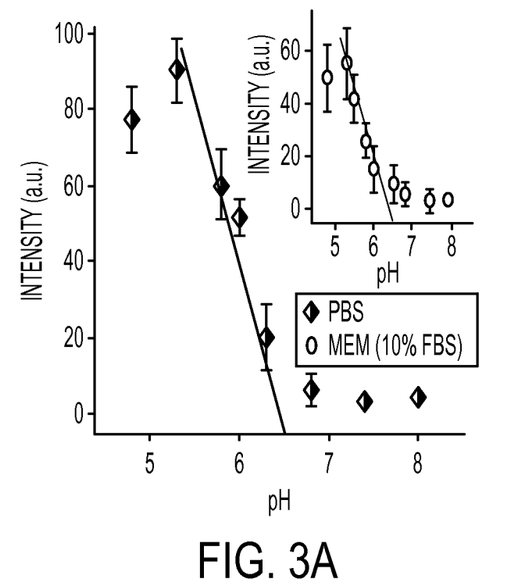

To obtain the curve of pH-dependent adsorption of GC-AuNPs onto a live cell membrane (FIG. 3, live cell imaging was performed at 25° C. in PBS at pHs 8.0, 7.4, 6.8, 6.3, 6.0, 5.8, 5.3, 4.8, or in 10% (v/v) FBS-containing MEM (without phenol red) at pHs 7.9, 7.4, 6.8, 6.5, 6.0, 5.8, 5.5, 5.3, 4.8. At each pH, cells were washed by PBS to remove cell culture medium and then rinsed with PBS or 10% (v/v) FBS-containing MEM at the specific pH to adjust the extracellular pH value. Fluorescence images were taken in such solution without GC-AuNPs but with the specific pH, and the intensity of cell membrane was measured as the autofluorescence background at this pH in PBS or in 10% (v/v) FBS-containing MEM. Subsequently, the solution was replaced by GC-AuNPs solution, and live cell images were taken after 5 min.

For each case (PBS or 10% (v/v) FBS-containing MEM with or without GC-AuNPs at a specific pH), 6 groups of fluorescence and bright-field images were taken. For each fluorescence image, the luminescent intensity of the cell membrane was measured from 6 different regions (autofluorescence background was subtracted) to give a mean value as the "intensity of cell membrane". The final result of "intensity of cell membrane" for each case was obtained from 6 fluorescence images and presented as mean±SD (n=6).

Figure 2A:
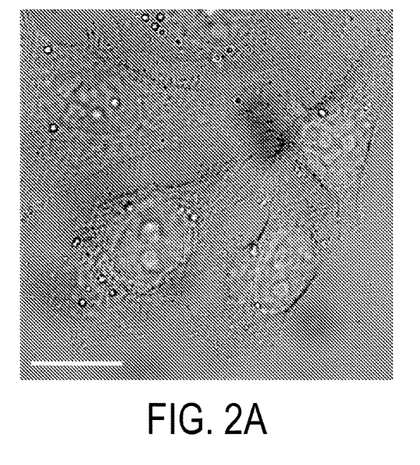
Figure 2B:
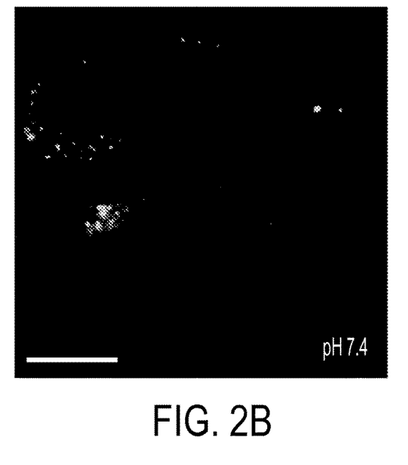
Figure 2C:
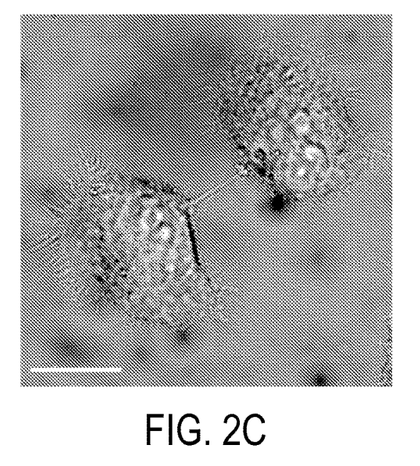
Figure 2D:
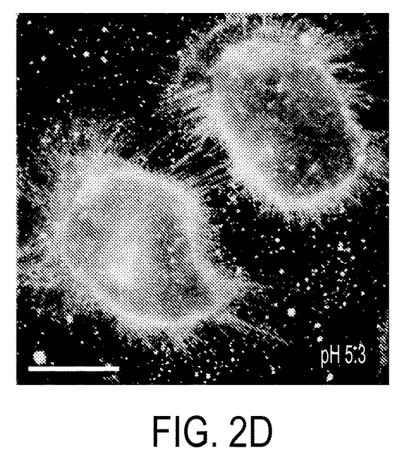
Figure 2E:
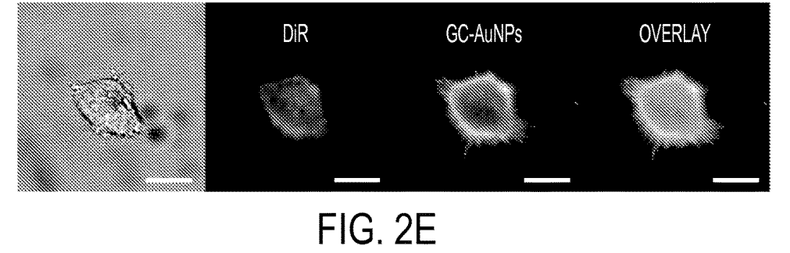

For colocalization experiment, the phospholipid bilayer membrane of live HeLa cells was first stained with DiR (2 μM, 37° C., 10 min) and then fluorescence image was taken in PBS (pH 5.3). After the fluorescence of DiR was completely photobleached by exposing to excitation light for 2 min, GC-AuNPs (in PBS, pH 5.3) was added on the cells, and then fluorescence image was taken subsequently (FIG. 2E).

To obtain three-dimensional luminescence imaging of live cells, HeLa cells were rinsed with PBS buffer and incubated with GC-AuNPs in PBS at pH 5.3 at 25° C., and then Z stack imaging was performed by an Applied Precision DeltaVision RT Deconvolution microscope (Applied Precision) with a 60× oil-immersion objective under Hg-lamp excitation (for fluorescence imaging, Ex: 541-569 nm; Em: 580-653 nm; 0.5 s exposure time). 45 xy sections were obtained at different z height and the distance between each xy section was 0.3 μm.

Fluorescence microscopy was used to probe the interactions between NPs and live cells and to investigate how the changes in the surface chemistry of the NPs and the local pH environment influence the NP-cell membrane interaction. Luminescent metal NPs are a class of new metal nanostructures that give intrinsic emission without the need of conjugation with fluorescent dyes. Therefore, potential interferences from organic dyes in the studies of surface chemistry effects on the NP-cell interactions can be circumvented. Glutathione, an abundant triamino acid peptide in nature, was chosen as a representative surface ligand due to its low affinity to serum proteins and the capability of minimizing nonspecific protein adsorption on the NPs. However, the glutathione-coated luminescent AuNPs (G-AuNPs) have very weak interaction with cells within a pH range from 5.3 to 7.4. To make the NP-cell membrane interaction pH dependent, in addition to glutathione, cationic cysteamine was also introduced into the luminescent AuNPs as the second surface ligand because protonated cysteamine can drive NPs to bind nonspecifically to the cell membrane through electrostatic attraction, which was also confirmed by our studies.

Figure 1A:
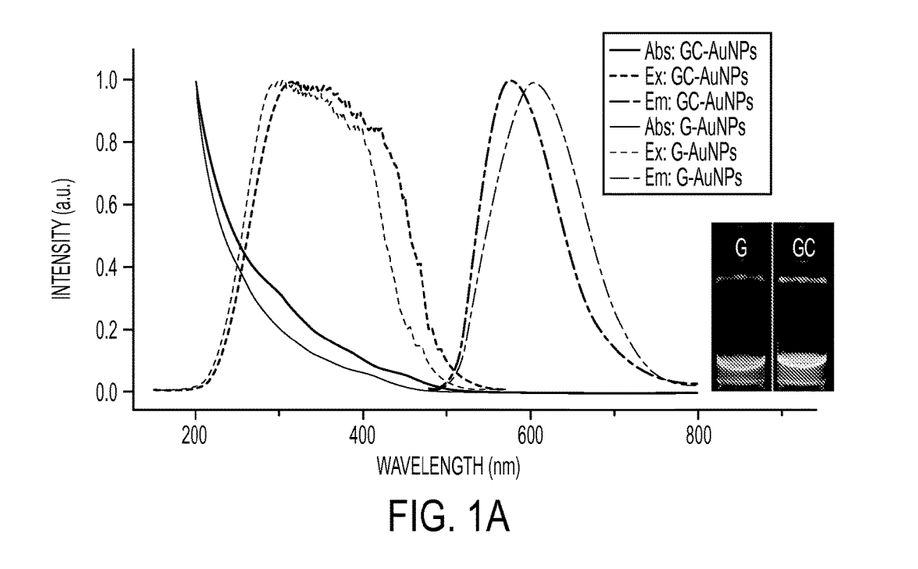
Figure 1B:
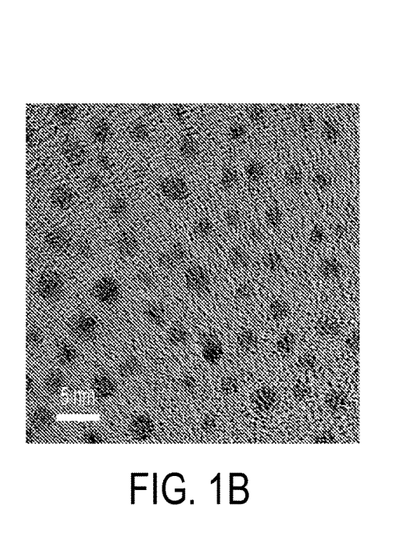
Figure 1C:
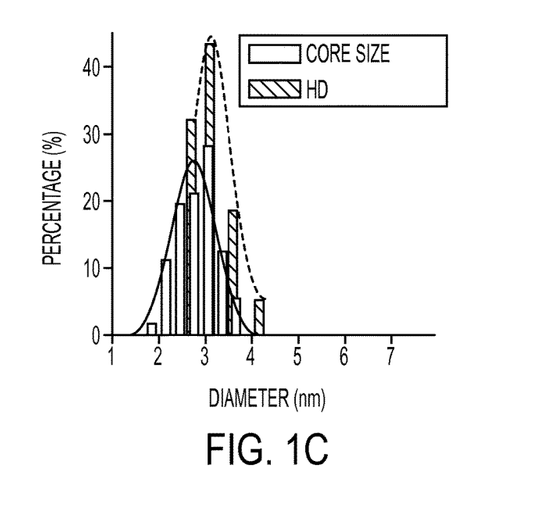

Glutathione and cysteamine-coated luminescent AuNPs (GC-AuNPs) were synthesized using a modified method that was used to create G-AuNPs. Briefly, a fresh aqueous solution (400 μL) containing 12.5 mM glutathione and 12.5 mM cysteamine was added into a 25 mM HAuCl4 aqueous solution (200 μL). Because of the strong Au(I)-S interaction, the two thiolated ligands immediately reacted with gold ions to form Au(I)-glutathione/cysteamine polymers, which dissociated into AuNPs naturally coated by glutathione and cysteamine. The FTIR analysis revealed the ratio of cysteamine to glutathione on the GC-AuNPs was approximately 10 to 7. The GC-AuNPs exhibited intensive yellow emission with a maximum at 575 nm and a quantum efficiency of about 9% in a pH range of 4.8-8.0, which is two times higher than that of G-AuNPs. The differences in the adsorption, excitation and emission spectra of G-AuNPs and GC-AuNPs indicated that the introduction of cysteamine enhances the emission property of luminescent AuNPs (FIG. 1A). The mean core size and hydrodynamic diameter of GC-AuNPs were 2.7±0.5 nm and 3.1±0.4 nm, respectively (FIGS. 1B, 1C), which are slightly larger than the ~2 nm G-AuNPs. While the positively charged cysteamine ligand in a mildly acidic environment can drive the AuNPs to bind nonspecifically to the cell membrane, cationic cysteamine coated-AuNPs became negatively charged in the presence of serum proteins, indicating that serious nonspecific protein adsorption on NPs occurred, consistent with a previous report. Therefore, to assess whether GC-AuNPs coated with both glutathione and cysteamine can still resist protein adsorption, the NPs were incubated in the absence or presence of fetal bovine serum at 37° C. for 30 min and then analyzed by agarose gel electrophoresis. GC-AuNPs displayed no changes in the mobility after incubation with fetal bovine serum at pH 7.4 and pH 5.3, suggesting that GC-AuNPs did not aggregate in the serum protein-containing medium and that serum proteins were not bound to the particles at neutral and mildly acidic pH values. In contrast, G-AuNPs started binding to proteins at pH 5.3, revealed by two luminescent bands after fetal bovine serum treatment. After the NPs were incubated with fetal bovine serum, additional protein staining by Coomassie brilliant blue 250 showed the blue protein band was well separated from the yellow band of GC-AuNPs at both pH 7.4 and pH 5.3, further confirming that GC-AuNPs have little interaction with serum proteins in the biological pH range from mildly acidic to neutral.

The pH-responsive membrane adsorption of GC-AuNPs in an extracellular pH range from 5.3 to 7.4 was investigated using fluorescence microscopy imaging of live HeLa cells as a model system. HeLa cells were also used in a previous study of pH-dependent insertion of a peptide because their membranes remain integral in the range of pH 5.5 to 7.4. As is shown in FIGS. 2A-D, GC-AuNPs had little interaction with cells at pH 7.4 in phosphate buffered saline (PBS). Once the extracellular pH was lowered to pH 6.0 and further dropped to 5.3, luminescence intensity of the cells increased dramatically, suggesting the adsorption of the NPs to the cell membrane was significantly enhanced in a slightly acidic environment. Z stack imaging of cells stained by GC-AuNPs at pH 5.3 indicated that the NPs were not internalized into the cells but bound on the cell surface, which was further confirmed by the colocalization of GC-AuNPs with DiR, a phospholipid bilayer membrane dye that can embed in the lipid bilayer (FIG. 2E). Due to the membrane adsorption, filopodia, the slender cytoplasmic projections for cell migration, was also clearly visualized at pH 5.3 using fluorescence microscopy, similar to membrane staining by DiR (FIG. 2D). Moreover, real-time imaging of live cells revealed that the accumulation of GC-AuNPs on the cell membrane reached a maximum within 30s, implying a fast membrane adsorption of the particles. These results clearly indicated that the additional surface ligand cysteamine made GC-AuNPs exhibit pH-dependent membrane adsorption in the biological pH range.

By quantifying the luminescence intensity of the cell membrane after incubation with GC-AuNPs at different pHs in PBS, the adsorption of GC-AuNPs onto live cell membranes was found to exponentially increase with the increase of $H^+$ concentration in the pH range of 4.8-8.0. Luminescence intensity of the cell membrane was increased about 28 times once the pH dropped from 7.4 to 5.3 (FIG. 3A). A similar pH-dependent membrane adsorption of GC-AuNPs was also observed in serum protein-containing cell culture medium. The pH thresholds for the membrane adsorption of GC-AuNPs in the absence or presence of serum proteins are 6.5 and 6.4 respectively (FIG. 3A), indicating that serum proteins did not interfere with the interaction of GC-AuNPs with the cells. This pH-dependent membrane adsorption of GC-AuNPs in the presence of serum proteins is attributed to a collaborative effect of glutathione and cysteamine ligands: glutathione prevents nonspecific protein adsorption while the positively charged cysteamine enables particles to nonspecifically bind to negatively charged cell membrane through electrostatic interactions.

Figure 3B:
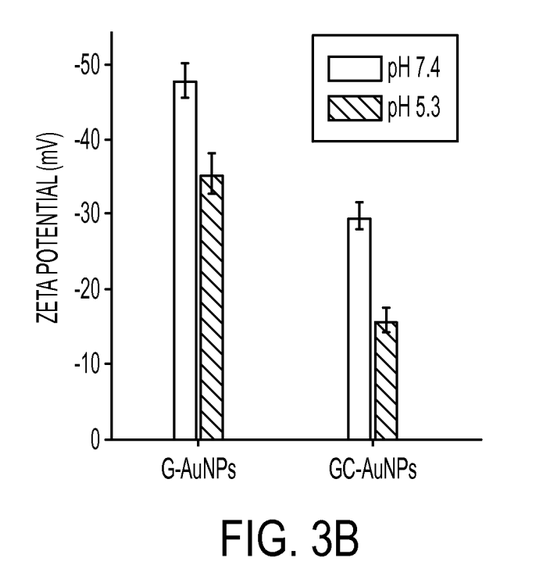

Both gel electrophoresis and zeta potential measurements have confirmed that GC-AuNPs are still negatively charged at pH 7.4 and pH 5.3 (Zeta potential: −29.76±1.81 mV and −15.71±1.71 mV, respectively, FIG. 3B). However, the zeta potentials of GC-AuNPs are much lower than those of G-AuNPs at the same pHs (−48.03±2.26 mV and −35.54±2.77 mV at pHs 7.4 and 5.3 respectively), suggesting that additional cysteamine ligand in the GC-AuNPs indeed significantly decreases the negative charge of the NPs. Since the cell membrane remains negatively charged at a pH above 5, the mildly acidic pH-triggered membrane binding of anionic GC-AuNPs implies that such pH-dependent adsorption behavior fundamentally arises from the decrease of global charge repulsion between GC-AuNPs and the cell membrane and an increase of attraction between protonated cysteamine ligand and the cell membrane. At pH 7.4, GC-AuNPs are still highly negatively charged; therefore, strong repulsion between the NPs and the cell membrane prevents the membrane adsorption. When the pH reached a critical point, ~pH 6.5, the threshold for adsorption, the local attraction between cysteamine and the membrane can overcome global electrostatic repulsion, and thus membrane adsorption of anionic GC-AuNPs onto negatively charged membranes started being observed.

Figure 4:
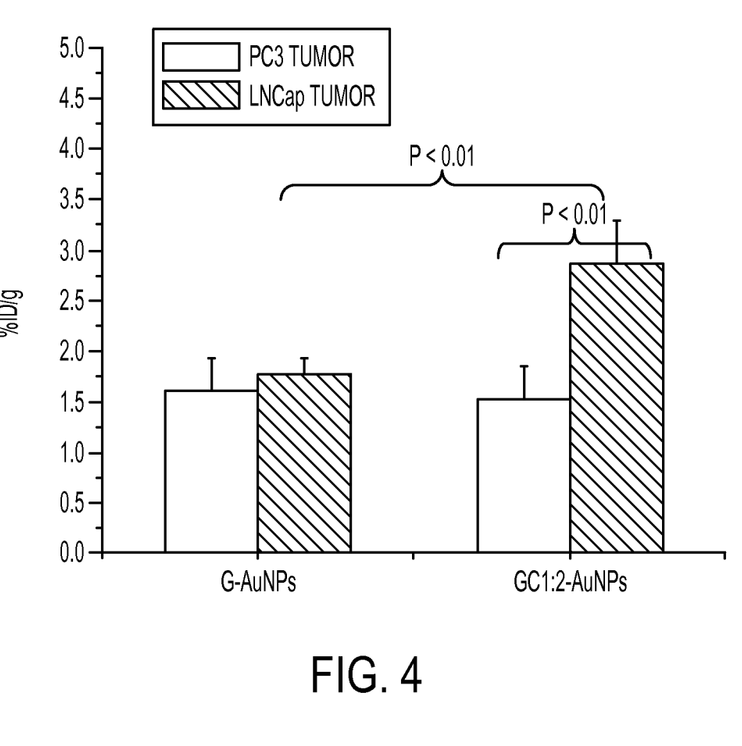
FIG. 4 shows a comparison of the accumulation of G-AuNPs and GC-AuNPs at tumor sites. LNCaP tumors are acidic tumors and PC3 tumors are non-acidic tumors. pH-responsive GC-AuNPs accumulated in the acidic tumors LNCaP tumors (pHe=6.8) two-fold better than in PC3 tumors (pHe=7.2), and two-fold better than pH nonresponsive G-AuNPs in both acidic and nonacidic tumors.

In experiments testing the ability of the GC-AuNPs to bind to tumor sites, it was shown that the GC-AuNPs were capable of binding to acidic as well as non-acidic tumors (FIG. 4). The GC-AuNPs were tested with LNCaP tumors (acidic) and PC3 tumors (non-acidic). As seen in FIG. 4, the accumulation of GC-AuNPs in LNCaP tumors was 2-fold higher than in PC3 tumors. The control non-pH responsive particles showed no difference in tumor uptake between LNCaP and PC3 tumors.

The observation that negatively charged GC-AuNPs are able to be bound to the negatively charged membrane seems against intuition but is consistent with recent molecular dynamic simulation on the nonspecific binding of anionic ~2 nm AuNPs to a negatively charged lipid membrane in a serum free environment and the experimental observation that anionic AuNPs with an ordered hydrophobic and hydrophilic surface structure can overcome the global repulsion between the NPs and the cell membrane and can cross negatively charged lipid membrane. By using a natural peptide, glutathione, and a simple aminothiol, cysteamine, as surface ligands, a negatively charged luminescent AuNP, which exhibits not only high resistance to nonspecific protein adsorption but also strong pH-dependent adsorption to live cell membranes within a biological pH range (5.3-7.4) has been synthesized. This simple surface chemistry strategy offers a new way to manipulate NP-cell membrane interactions in a native biological environment. Considering that pH plays a key role in many cellular processes and is an indicator for a pathological environment, metal NPs with pH-dependent membrane adsorption might find new applications in tumor diagnosis and therapy.

Although the present invention has been described in connection with some embodiments, it is not intended to be limited to the specific form set forth herein. Rather, the scope of the present invention is limited only by the accompanying claims. Additionally, although a feature may appear to be described in connection with particular embodiments, one skilled in the art would recognize that various features of the described embodiments may be combined in accordance with the invention. In the claims, the term comprising does not exclude the presence of other elements or steps.

Furthermore, although individually listed, a plurality of means, elements or method steps may be implemented by e.g. a single unit or processor. Additionally, although individual features may be included in different claims, these may possibly be advantageously combined, and the inclusion in different claims does not imply that a combination of features is not feasible and/or advantageous. Also, the inclusion of a feature in one category of claims does not imply a limitation to this category but rather indicates that the feature is equally applicable to other claim categories as appropriate. Furthermore, the order of features in the claims do not imply any specific order in which the features must be worked and in particular the order of individual steps in a method claim does not imply that the steps must be performed in this order. Rather, the steps may be performed in any suitable order. In addition, singular references do not exclude a plurality. Thus references to "a", "an", "first", "second" etc do not preclude a plurality.

What is claimed is:

1. A composition comprising a fluorescent noble metal nanoparticle, said nanoparticle comprising a noble metal core, wherein the surface of the noble metal core is coated with a glutathione and cysteamine or a cysteamine analog at a glutathione-to-cysteamine/cysteamine analog ratio of from 1:2.5 to 1:1, wherein the noble metal nanoparticle is defined as comprising between 2 and 1000 noble metal atoms, or having a diameter of 0.3 nm to 3 nm, and wherein the noble metal nanoparticle binds to a molecule of interest on a tumor cell in an acidic tumor microenvironment defined by a pH of between 5.3 and 7.0.

2. The composition of claim 1, wherein the noble metal nanoparticle comprises between 2 and 1000 noble metal atoms.

3. The composition of claim 1, wherein the noble metal is selected from the group consisting of gold, silver, and copper.

4. The composition of claim 1, wherein the nanoparticle further comprises a pH-dependent peptide.

5. The composition of claim 4, wherein the pH-dependent peptide comprises pH low insertion peptide (pHLIP).

6. A method of detecting a surface of a tumor cell in an acidic microenvironment, the method comprising the steps of:
    (a) contacting the composition of claim 1 with a surface of a tumor cell;
    (b) adsorbing the composition comprising fluorescent noble metal nanoparticles on to the surface of the tumor cell; and
    (c) detecting the presence of the fluorescent nanoparticle on the surface of the tumor cell.

7. The composition of claim 5, wherein the pHLIP comprises the sequence of SEQ ID NO: 1.

8. The composition of claim 1, wherein the acidic tumor microenvironment defined by a pH of between 5.3 and 6.5.

9. The method of claim 6, wherein the acidic tumor microenvironment defined by a pH of between 5.3 and 6.5.

10. The composition of claim 1, wherein the noble metal nanoparticle has a diameter of 0.3 nm to 3.0 nm.

11. The method of claim 6, wherein the noble metal nanoparticle has a diameter of 0. 3 nm to 3.0 nm.

12. The method of claim 6, wherein the noble metal nanoparticle comprises between 2 and 1000 noble metal atoms.

13. The method of claim 6, wherein the noble metal is selected from the group consisting of gold, silver, and copper.

14. The method of claim 6, wherein the nanoparticle further comprises a pH-dependent peptide.

15. The method of claim 14, wherein the pH-dependent peptide comprises pH low insertion peptide (pHLIP).

16. The method of claim 15, wherein the pHLIP comprises the sequence of SEQ ID NO: 1.

* * * * *